United States Patent [19]

Ohashi et al.

[11] Patent Number: 4,725,539

[45] Date of Patent: Feb. 16, 1988

[54] METHOD FOR ANALYZING PLURAL OXIDIZABLE COMPONENTS IN A LIQUID

[75] Inventors: Minoru Ohashi; Nobuhiko Arakawa, both of Tokyo; Osamu Oka, Kawagoe; Kenichi Numazawa, Ageo; Yoshio Utugi, Hiki, all of Japan

[73] Assignees: Oriental Yeast Co. Ltd.; Oriental Electric Co. Lt., both of Japan

[21] Appl. No.: 584,347

[22] Filed: Feb. 28, 1984

[30] Foreign Application Priority Data

Mar. 8, 1983 [JP] Japan .................................. 58-36736

[51] Int. Cl.$^4$ .......................... C12Q 1/62; C12Q 1/48; C12Q 1/42; C12Q 1/26
[52] U.S. Cl. ........................................ 435/10; 435/15; 435/21; 435/25
[58] Field of Search ................... 435/4, 10, 14, 18, 21, 435/25, 22, 15

[56] References Cited

U.S. PATENT DOCUMENTS

| | | | |
|---|---|---|---|
| 3,879,263 | 4/1975 | Adams | 435/22 X |
| 4,040,908 | 8/1977 | Clark, Jr. | 435/25 X |
| 4,317,878 | 3/1982 | Nakanishi et al. | 435/10 |
| 4,416,982 | 11/1983 | Tsuda et al. | 435/14 X |
| 4,550,078 | 10/1985 | Yamada et al. | 435/25 |

FOREIGN PATENT DOCUMENTS

| | | | |
|---|---|---|---|
| 0159513 | 10/1985 | European Pat. Off. | 435/4 |
| 0149050 | 11/1980 | Japan | 435/4 |
| 0097863 | 8/1981 | Japan | 435/22 |
| 0177699 | 11/1982 | Japan | 435/22 |
| 80/00454 | 3/1980 | World Int. Prop. O. | 435/25 |
| 2078369 | 1/1982 | United Kingdom | 435/4 |

OTHER PUBLICATIONS

Chemical Abstracts, vol. 96, Abstract No. 177337y, (1982), Imai et al.
Chemical Abstracts, vol. 95, Abstract No. 38619h, (1981), Tawa et al.
Chemical Abstracts, vol. 98, Abstract No. 177577t, (1983), Watanabe et al.
Price et al, Preparation of Nucleoside Phosphorplase from Calf Spleen, In: Methods in Enzymology, Colowick et al, (edit), vol. II, Academic Press, New York, 1955, pp. 448-453.
Cammann, Karl, *Das Arbeiten mit ionenselektiven Elektroden* (pp. 98-106) Berlin, Heidelberg, New York: Springer-Verlag, 1977. (translation included).

*Primary Examiner*—Robert J. Warden
*Assistant Examiner*—Randall E. Deck
*Attorney, Agent, or Firm*—Stevens, Davis, Miller & Mosher

[57] ABSTRACT

A new method of rapidly analyzing plural substances in the presence of biological catalyzers is disclosed. The method is practiced by way of the steps of injecting both pH buffer solution and specimen into a reaction cell, successively adding a plurality of enzymes to induce uptake reaction of dissolved oxygen, causing the plurality of substances to be subjected to selective oxidation in the stepwise manner, obtaining a stepdown curve of dissolved oxygen by automatically recording the oxidative process by means of a dissolved oxygen sensor, qualitatively determining each of the substances with reference to the kind of added enzymes and the order of their addition and quantitatively determining the same with reference to the extent of decrease in dissolved oxygen. Typically, oxidation of the substances is carried out by way of two or three or further more steps. The reaction cell for performing the method is equipped with a dissolved oxygen sensor on the one side wall and its upper portion is airtightly closed with a plug through which a fine bore is formed for the purpose of supply of buffer solution, specimen and enzymes.

2 Claims, 4 Drawing Figures

4,725,539

METHOD FOR ANALYZING PLURAL OXIDIZABLE COMPONENTS IN A LIQUID

BACKGROUND OF THE INVENTION

1. Field of the Invention

The present invention relates to a method of rapid analysis of plural components and more particularly to a method of bioelectrochemically analyzing biological substances or foodstuff substances such as amino acids, nucleic acids, saccharides, lipids or the like.

2. Description of the Prior Art

As a typical conventional method of separation analysis on amino acids, nucleic acids, saccharides, lipids, vitamins or the like, chromatographic method has been hitherto employed. However, it is pointed out as drawbacks inherent to the conventional method that it takes a long time to separate each of components from one another and moreover a number of reagents and a high level of skill are required. Further, another drawback of the conventional method is that an apparatus required for performing the method is complicated in structure and it is manufactured at an expensive cost.

In recent years an improved method of determining only a specific component among plural ones easily, rapidly and selectively with the aid of an electrochemical sensor such as oxygen electrode, hydrogen peroxide electrode with biological catalyzers such as enzyme, biological cell or the like has been proposed (see Koteikakoso, Immobilized Enzymes (1977), edited by Ichiro Chibata and published by Kodansha Scientific Co., Ltd.). However, it is found that the improved method fails to simultaneously analyze plural components.

SUMMARY OF THE INVENTION

Hence, the present invention has been made with the foregoing drawbacks in mind and its object resides in providing a method of simultaneously analyzing plural components rapidly and easily.

To accomplish the above object, there is proposed, in accordance with the present invention, a method of rapidly analyzing plural components essentially comprising the steps of filling pH buffer solution and liquid to be tested into a reaction cell which is designed so as not to allow air to enter therein from the outside, adding plural biological catalyzers one after another, said biological catalyzers being effective for inducing uptake reaction of dissolved oxygen, causing the plural components to be selectively oxidized in the stepwise manner, obtaining a stepdown curve of dissolved oxygen by automatically recording the oxidative process with the aid of a sensor, qualitatively detecting each of the components with reference to the kind of added biological catalyzers and the order of their addition, and quantitatively determining the same with reference to the extent of decrease in dissolved oxygen.

In order to assure that the method of the invention is satisfactorily practiced it is necessary to provide an apparatus for continuously measuring and recording dissolved oxygen. As a sensor required for the apparatus, any conventional sensors such as polarographic membrane-covered oxygen electrode that is called Clark electrode, galvanic cell type dissolved oxygen electrode, oxygen pressure balancing type oxygen electrode which has been lately invented by Connery or the like sensor is employable.

Further, it is necessary to provide a reaction cell with a dissolved oxygen sensor inserted therein or fitted thereto in which any change of dissolved oxygen in reaction liquid can be exactly measured without any entrance of oxygen from the outside and into which reagent, catalyzer and others can be added as required for the purpose of controlling reaction.

Other objects, features and advantages of the present invention will be more clearly apparent from reading of the following description which has been prepared in conjunction of the accompanying drawings.

BRIEF DESCRIPTION OF THE DRAWINGS

The accompanying drawings will be briefly described below.

DESCRIPTION OF THE PREFERRED EMBODIMENTS

Figure 1:
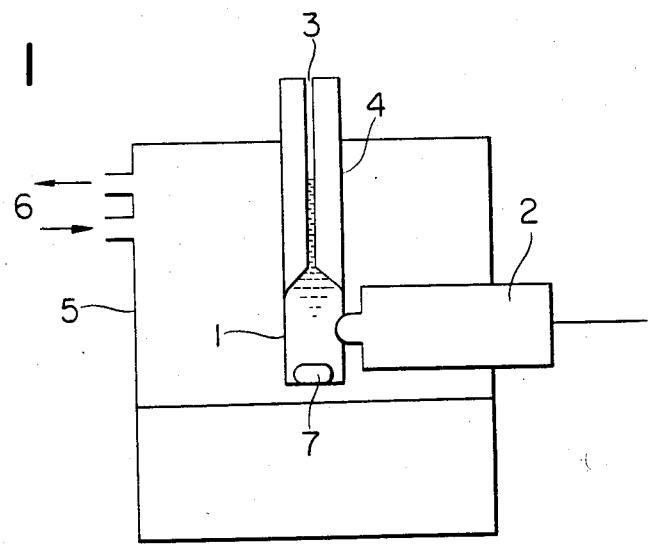
FIG. 1 is a schematic sectional side view illustrating a reaction cell for performing the method of the invention.

In order to readily understand the present invention preferred embodiments will be described below with reference to the accompanying drawings. FIG. 1 schematically illustrates an example of apparatus for performing the method of the invention. The apparatus includes a reaction cell 1 having a capacity of about 2 ml and a dissolved oxygen sensor 2 (hereinafter referred to simply as DO sensor) fixedly sedured to the one side wall of said reaction cell 1. Further, the upper part of the reaction cell 1 is air-tightly capped with a plug 4 through which a fine bore 3 is provided so that air is prevented from entering into the reaction cell 1 from the outside. Thus, a required volume of reaction control agent can be filled into the reaction cell 1 through said fine bore 3 with the aid of a microsyringe or the like device. Reaction temperature is controlled by circulating water 6 throughout the jacket 5 while it is kept at a constant temperature, and reaction liquid is well mixed and stirred with the aid of a magnetic stirrer 7. It should be noted that the present invention should not be limited only to the above-described apparatus and the latter may be changed or modified in any other acceptable manner.

Next, as biological catalyzer for the invention hydrolase such as invertase, amylase or the like and oxidase such as glucose oxidase (hereinafter referred to as G.O.D.) or the like are employable for the purpose of analyzing saccharides, proteases, peptidases and amino acid oxidases are employable for the purpose of analyzing protein and amino acid, and cholesterol esterase and cholesterol oxidase are employable for the purpose of analyzing cholesterol. Further, nucleotidase, nucleosido phosphorylase, xanthin oxidase or the like are employable for the purpose of determining nucleic acid relating substances, for instance, inosinic acid which is obtainable from decomposition of adenosine triphosphate.

It should be noted that dehydrogenase with which there does not occur oxygen uptake reaction, for instance, lactic acid dehydrogenase, alcohol dehydrogenase or the like are employable for analyzing lactic acid, alcohol or the like in the presence of coenzyme and auxiliary agent such as phenazine methasulfate or the like serving as hydrogen transfer agent. In some case biological cell may be employable for the above-mentioned purposes.

Operations for analyzing plural components at the highest efficiency in accordance with the method of the invention can be performed in various manners. As a preliminary step prior to performing the aforesaid operation it is recommended that reaction characteristics inherent to a single substance among them are previously examined with reference to standard sample, provided that the existence of said substance is known. For instance, conditions for allowing a required oxidation reaction to proceed quickly are confirmed in comparison with slope of oxygen uptake curve while varying quantity of enzyme, pH of reaction solution, composition of buffer solution, temperature and others.

Incidentally, qualitative analysis may be carried out by making determination as to which oxidase and relating biocatalyzers among those added one after another for several substances of which existence is expected is attributable to occurence of oxygen uptake, wherein said determination is assisted by observing whether the oxygen uptake curve is extended downwardly of not.

Since an extent of decrease in output obtained by measurements at two time points corresponds to concentration of a substance which responses to the function of added catalyzer, one of said time points being before said catalyzer is added and the other one being when oxygen uptake reaction (leading to reduction of dissolved oxygen) comes to a stop, quantitative as well as qualitative analysis can be carried out at the same time.

It should be noted that an extent of decrease in output can be converted to a value of dissolved oxygen by obtaining oxygen solubility at a measuring temperature with the aid of a table (for instance, see Section "Dissolved Oxygen" in Testing Method for Industrial Water (JIS K 0101) and Testing Method for Waste Water (JIS K 0102) after a certain buffer solution saturated with air is filled into the reaction cell and output from the sensor is then measured. Thus, an amount of oxygen consumption can be obtained with respect to an unit amount of standard sample by comparing the known concentration of standard sample with an amount of decrease in dissolved oxygen. Accordingly, it is possible to know concentration of the substance immediately from the amount of oxygen consumption without any use of standard solution.

It should be noted that when a substance in which no decrease in dissolved oxygen is analyzed, for instance, sucrose which is not subjected to action of glucose oxidase as long as there is provided no preliminary reaction, selection is made for such a preliminary reaction so as to allow invertase, which is a hydrolase, for converting sucrose to glucose which is then oxidized.

Next, the reaction mixture solution of glucose and sucrose is added with enzymes in accordance with the order of glucose oxidase→invertase so that a dissolved oxygen stepdown curve having two steps is obtained. Thus, concentration of glucose can be obtained from the descent extent across the first step, whereas concentration of sucrose can be obtained from the descent extent across the second step. Preliminary reaction as described above may be carried out by way of two steps or three steps or further more steps as required, using hydrolase, transfer enzyme or the like.

Further, a plurality of oxidases may be used for preliminary reaction. Thus, a proper combination of above-described reactions makes it possible to determine a number of substances either qualitatively or quantitatively.

Now, the present invention will be described in more details below with respect to a few examples.

EXAMPLE 1

Analysis of mixed solution of hypoxanthin (hereinafter referred to simply as $H_x$) and xanthin (hereinafter referred to simply as X)

1. Principle of the reaction for analysis

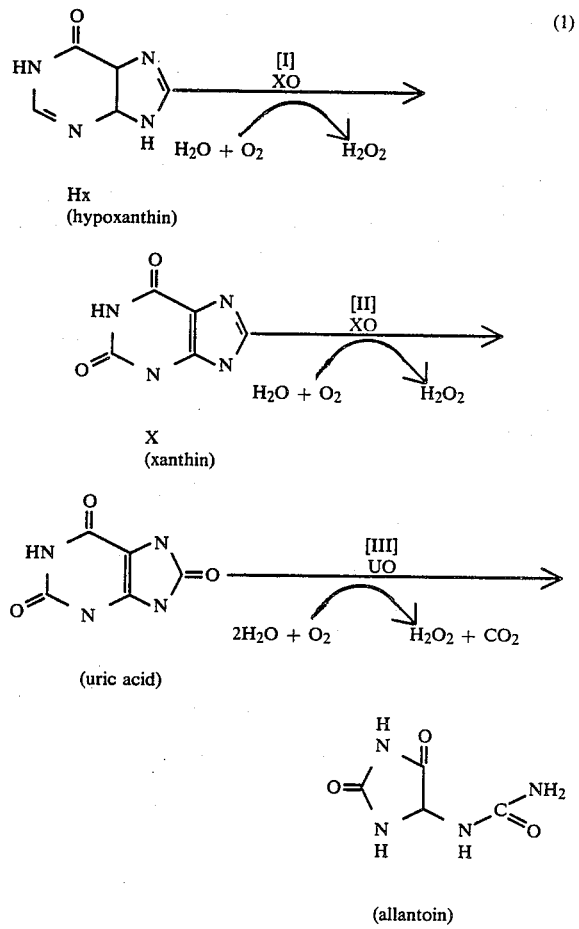

where reference symbol XO designates xanthin oxidase and reference symbol UO does uricase.

2. Apparatus and material used (1) DO sensor: Clark type electrode which has 3 mm diameter platinum cathode, covered with FEP film having a thickness of 1/1000 inch (manufactured by Oriental Electric Co., Ltd.). When the sensor is in use, 0.7 volt D.C. is applied.

(2) Recorder: It was manufactured by Shimazu Manufacturing Co., Ltd. It had a full scale of 100 mV and it is adapted to operate at a recording rate of 1 cm/min.

(3) Reaction cell: It was controlled to maintain a constant temperature of 37° C. and it had a capacity of 2,000 μl.

(4) Enzyme: XO was used at a rate of 0.4 I.U/ml in the form of 3.2M ammonium sulfate suspension (made by Boehringer Mannheim AG). On the other hand, UO was used at a rate of 0.41 I.U/ml in the form of 50 mM boric acid buffer solution (made by Oriental Yeast Co., Ltd.).

(5) Buffer solusion: It was prepared in the form of 1/15M phosphate buffer solution (pH 7.6) saturated with air at a temperature of 37° C. (P.B.S.). Further, it had concentration of dissolved oxygen of 0.214 μmol/ml (at a temperature of 37° C.).

(6) Liquid to be tested:
$H_x$: 10 μmol (1.36 mg)/ml
X: 10 μmol (1.52 mg)/ml
$H_x$, X: mixture solution of both substances 3. Operations (see FIGS. 2 and 3)

Figure 2:
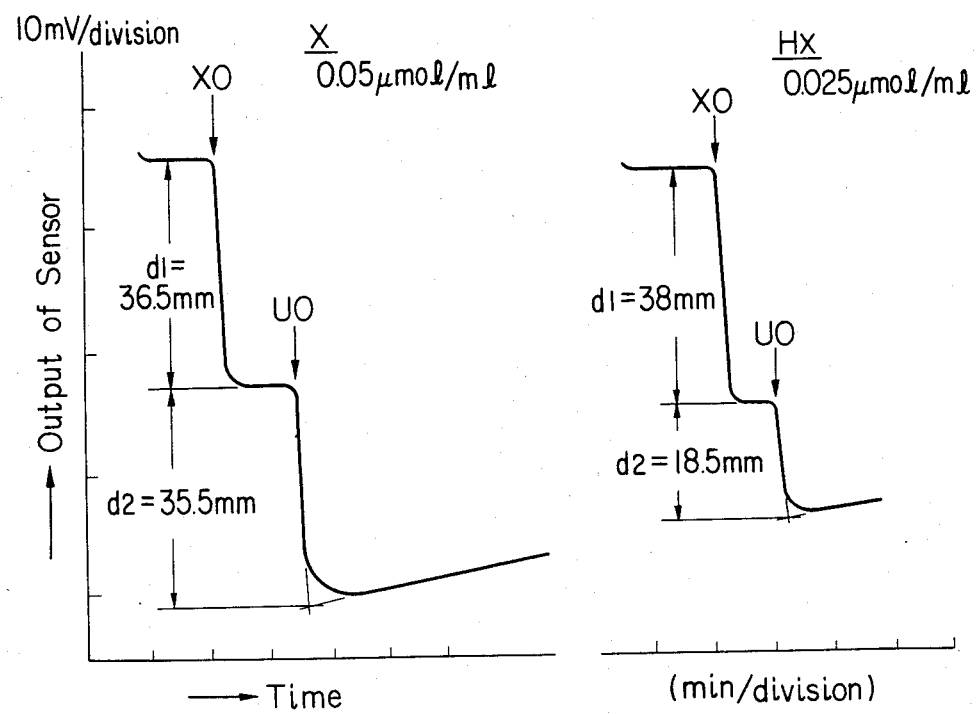
FIG. 2 is a stepdown curve of dissolved oxygen produced during analysis of xanthin (X) and hypoxanthin (Hx).

A volume of appreciably more than 2000 μl of P.B.S. was filled in the reaction cell as illustrated in FIG. 1 and capped with a plug (to such a level that a part of solution was raised upto the lower end of the fine bore 3. Then, liquid of X and $H_x$ to be tested (5 μl or 10 μl in volume) was taken into a microsyringe and thereafter it was injected into the reaction cell through the fine bore 3 while it was stirred. Next, a volume of 20 μl of XO was also injected into the reaction cell and then after it was confirmed by observing a decrease in output of the DO sensor as identified with reference letter $d_1$ in FIG. 2 that the decrease in output from the sensor came to a stop, a volume of 20 μl of UO was added immediately whereby a dissolved oxygen stepdown curve including two steps as illustrated in FIG. 2 was obtained.

Figure 3:
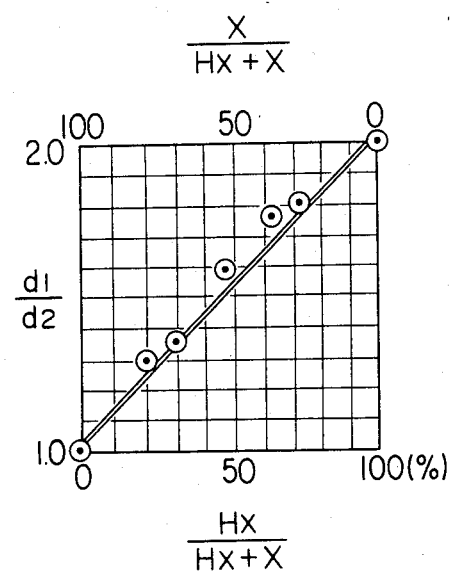
FIG. 3 is a correlation curve illustrating the relation between ratio of xanthin and hypoxanthin concentration and decrease ratio ($d_1/d_2$) in output current generated during oxidative reaction comprising two steps with xanthin oxidase and uricase.

FIG. 3 diagrammatically illustrates a relation between composition ratio of unit liquid to mixed solution and stepdown ratio, that is, $d_1/d_2$. As is apparent from the drawing, stepdown ratio is linearly related to mixing ratio of the mixed solution because the characteristic curve is linearly extended through two points, one of them being such that $d_1/d_2 = 1$ is established with 100% X and the other one being such that $d_1/d_2 = 2$ is established with 100% $H_x$.

Incidentally, when a relation between decrease in dissolved oxygen and concentration of substrate was examined, it was found that a volume of oxygen $O_2$ in mol absorbed by addition of UO was related equally to concentration of substrate with respect to either X or $H_x$.

Table 1 Relation between concentration of X and $H_x$ and volume of consumed oxygen $O_2$

| substance | Substrate (composition to be analyzed) in $\frac{\mu mol}{ml}$ concentration C during reaction | Volume of absorbed oxygen $O_2$ in $\frac{\mu mol}{ml}$ |
|---|---|---|
| X | 0.05 | 0.054 |
| $H_x$ | 0.25 | 0.028 |

Thus, mol concentration of ($H_x$+X) is obtainable from $d_2$ of the mixture solution of X and $H_x$ and moreover its volume ratio is obtainable with reference to FIG. 3. As a result, the concentration of each of the substances can be obtained.

Each of the substances is a kind of intermediate metabolite which is excreted in the form of uric acid after decomposition of adenosine triphosphate in animal body and therefore establishment of a method of separating and quantitatively determining them will highly contribute to biochemical industry, foodstuff industry and their associated industries. As is well known, their fractional quantitative determination is achieved only with much difficulties with the aid of any of conventional methods including chromatographic method and conventional enzymatic method (which is normally carried out by optical detection and determination). As will be readily understood from FIG. 2, however, the method of the invention makes it possible to quantitatively determine each of the substances at high accuracy within a short period of time shorter than 5 minutes without necessity for standard liquid.

EXAMPLE 2

Quantitative determination of substance obtained from decomposition of adenosine triphosphate In this example description will be made as to fractional quantitative determination among inosinic acid (hereinafter referred to simply as IMP), inosine (hereinafter referred to as simply $H_xR$) and hypoxanthin (hereinafter referred to simply as $H_x$).

1. Principle of the reaction for analysis

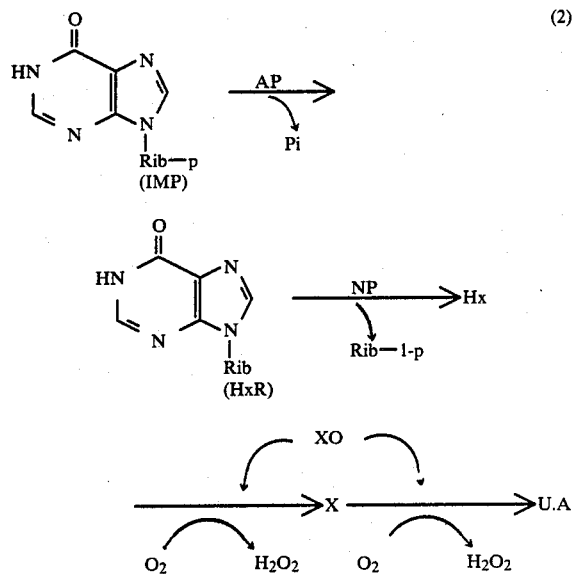

where
reference symbol AP designates alkali phosphatase,
reference symbol NP does nucleoside phosphorylase,
reference symbol UA does uric acid,
reference symbol Rib does ribose and
reference symbol Pi does inorganic phosphate.

2. Apparatus and material used
   (1) DO sensor
   (2) Recorder
   (3) Reaction chamber The same apparatuses (1) to (3) as those in Example 1 were used for this example under the same operating conditions.

(4) Enzyme

AP was prepared in the form of 3.2M ammonium sulfate suspension and it was used at a rate of 65 I.U/ml (at a temperature of 37° C.). NP was prepared in the form of 3.2M ammonuium sulfate suspension and it was used at a rate of 20 I.U/ml (at a temperature of 25° C.). XO was prepared in the form of 3.2M ammonium sulphate suspension and it was used at a rate of 0.4 I.U/ml. Each of the enzymes as mentioned above is a product produced by Boehringer Mannheim AG.

(5) Buffer solusion

A liquid was prepared in the form of 1/15M glycine-NaOH buffer solution (having pH 10.5). Further, 2 μl of 0.1M $ZnCl_2$ and 2 μl of 0.1M $MgCl_2$ were added to a volume of 2 ml of A liquid as mentioned above.

B liquid was prepared in the form of 1/15M phosphate buffer solution in the same manner as in the foregoing example.

(6) Liquid to be tested

A volume of 4 μl of mixed solution (10 μmol/ml) comprising IMP, $H_xR$ and $H_x$ each of which was mixed together by the same volumetric rate was used for the experiment.

Figure 4:
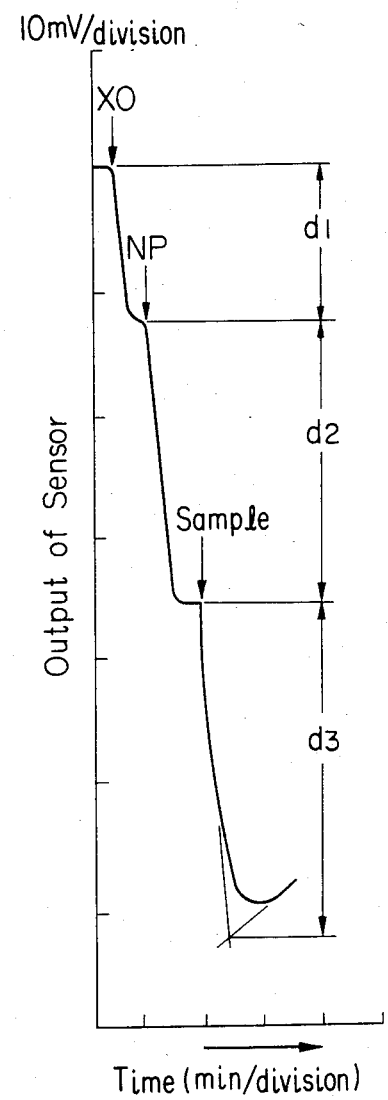
FIG. 4 is a stepdown curve of dissolved oxygen during oxidative reaction comprising three steps for analyzing the mixture liquid of inosinic acid, inosine and hypoxanthin.

3. Operations (see FIG. 4)

Operations can be carried out by way of various types of steps. Now, an example of typical simple process of operations with the minimized quantity of enzyme used therefor will be shown on the following flow sheet.

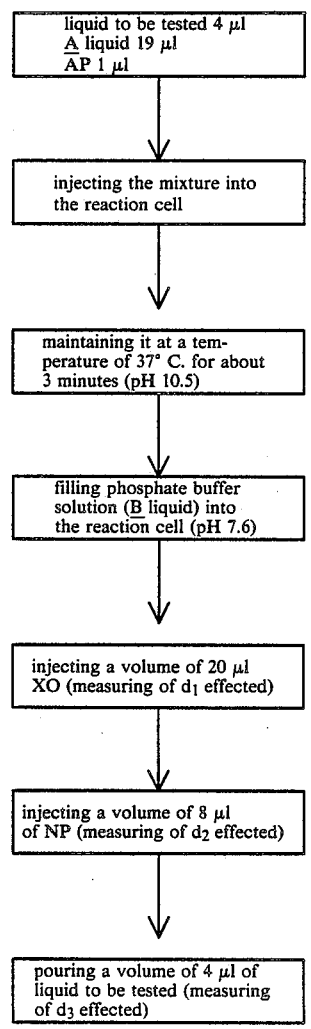

4. Calculation of concentration $$C_{Hx} = \frac{d_1}{d_0} \times 0.107 \text{ (μ mol/ml)} \quad (3)$$

$$C_{IMP} = \frac{(d_1 + d_2 - d_3)}{d_0} \times 0.107 \text{ (")} \quad (4)$$

$$C_{HxR} = \frac{(d_3 - d_1)}{d_0} \times 0.107 \text{ (")} \quad (5)$$

where reference symbol $d_0$ designates recorder span (mm) corresponding to output of water saturated with air and reference symbols $C_{Hx}$, $C_{IMP}$ and $C_{HxR}$ are the concentrations (μmol/ml) of $H_x$, IMP and $H_xR$.

The principle on which concentration of each of the substances can be obtained from the above-noted calculations will be readily understood on the basis of the reaction formula (2) by any expert in the art, but in view of the fact that each of the substances absorbs oxygen $O_2$ by 2 mol per 1 mol of the former a coefficient of 0.214/2=0.107 was used for calculations. Since IMP and $H_xR$ do not absorb oxygen in the presence of XO, it will be obvious that $C_{Hx}$ can be obtained with the aid of Equation (3). Next, with respect to reaction corresponding to $d_2$ $C_{(IMP+HxR)}$ can be obtained because $H_x$ has disappeared by addition of XO. Therefore, it results that $(d_1+d_2)$ corresponds to the number of mol of all substances. Further, with respect to reaction corresponding to $d_3$ initially added substance has disappeared and since the pH is neutral, AP fails to exhibit its activity and therefore substances excluding IMP can be detected. Thus, concentration of IMP can be obtained from difference between $(d_1+d_2)$ and $d_3$ using Equation (4). Incidentally, no particular description will be required as to calculation of $C_{HxR}$.

Finally, features and advantages of the present invention will be summarized below.

(1) Preliminary treatment is easy to be carried out for specimen without any influence of coloring, turbidity, absorbability of ultraviolet ray and others of liquid to be tested.

(2) Measurements are made very rapidly.

(3) Excellently high specificity is assured.

(4) An apparatus for practicing the method can be designed very simply.

(5) Measurements can be made at a low concentration in the range of 0.005 to 0.1 μmol/ml with excellent high sensibility.

(6) A quantity of consumption of enzyme can be minimized by using a small reaction cell. As described in Example 2, enzyme which has once added can be used repeatedly (for instance, XO can be used three times and NP can be used two times).

(7) All operations are performed at a room temperature with high safety because of no necessity for dangerous chemicals.

As will be readily understood from the above description, the method of the present invention has many adventageous features as noted above and therefore it very useful for analysis of various substances as mentioned above.

While the present invention has been described above only with respect to typical embodiments and examples, it should of cource be understood that it should not be limited only to them but various changes or modifications may be made without any departure from the spirit and scope of the invention.

What is claimed is:

1. A method for analyzing inosinic acid, inosine and hypoxanthine in a liquid containing them, which comprises the steps:
    (a) adding a volume of the liquid and pH buffer solution at a pH of 10.5 to a reaction cell designed to prevent air from entering the cell, said reaction cell being equipped with an oxygen sensor connected to an automatic recording device,
    (b) adding alkaline phosphatase enzyme to catalyze the hydrolysis of inosinic acid to inosine,
    (c) adjusting the pH of said liquid to neutrality and adding xanthine oxidase enzyme to catalyze the oxidation of hypoxanthine to xanthine,
    (d) recording oxygen sensor output,
    (e) adding nucleoside phosphorylase enzyme to catalyze the conversion of inosine to hypoxanthine, the xanthine oxidase enzyme present catalyzing the oxidation of the thus formed hypoxanthine to xanthine,
    (f) recording oxygen sensor output,
    (g) adding a volume of the liquid identical to that added in step a, the nucleoside phosphorylase and the xanthine oxidase enzymes present catalyzing the conversion of the inosine added to hypoxanthine and the oxidation of the hypoxanthine added and that thus formed to xanthine,
    (h) recording oxygen sensor output, and
    (i) calculating the amount of hypoxanthine present from the decrease in oxygen sensor output in step d, calculating the amount of inosinic acid present from the decrease in oxygen sensor output in steps d plus f less the decrease in oxygen sensor output in step h, and calculating the amount of inosine present from the decrease in oxygen sensor output in step h less the decrease in oxygen sensor output in step d.

2. A method for analyzing hypoxanthine and xanthine in a liquid containing them, which comprises the steps:
    (a) adding a volume of the liquid to a reaction cell designed to prevent air from entering the cell, said reaction cell being equipped with an oxygen sensor connected to an automatic recording device,
    (b) adding xanthine oxidase to catalyze the oxidation of hypoxanthine and xanthine to uric acid,
    (c) recording oxygen sensor output,
    (d) adding uricase to catalyze the oxidation of uric acid to allantoin,
    (e) recording the oxygen sensor output,
    (f) calculating the ratio of decrease in oxygen sensor output in step (c) to decrease in oxygen sensor output in step (e), and
    (g) determining the amounts of hypoxanthine and xanthine present in the liquid from a graph wherein ratios of decrease in oxygen sensor output in step (c) to decrase in oxygen sensor output in step (e) in mixtures containing known amounts of hypoxanthine and xanthine are plotted against the amounts of hypoxanthine and xanthine present in known mixtures.

* * * * *